United States Patent [19]

Rasmusson et al.

[11] 4,377,584
[45] Mar. 22, 1983

[54] 4-AZA-17β-SUBSTITUTED-5α-ANDROSTAN-3-ONE-REDUCTASE INHIBITORS

[75] Inventors: Gary H. Rasmusson, Watchung; David B. R. Johnston, Warren, both of N.J.; Glen E. Arth, deceased, late of Cranford, N.J., by Rose B. Arth, executrix

[73] Assignee: Merck & Co., Inc., Rahway, N.J.

[21] Appl. No.: 189,981

[22] Filed: Sep. 23, 1980

Related U.S. Application Data

[63] Continuation-in-part of Ser. No. 20,371, Mar. 15, 1979, abandoned, which is a continuation-in-part of Ser. No. 896,118, Apr. 13, 1978, abandoned.

[51] Int. Cl.³ .............. A61K 31/395; A61K 31/47; C07D 221/18
[52] U.S. Cl. .................. 424/258; 260/239 BB; 260/239.3 P; 424/244; 546/77; 546/78
[58] Field of Search ............ 546/77, 78; 260/239 BB, 260/239.3 P; 424/244, 258

[56] References Cited

U.S. PATENT DOCUMENTS

| | | |
|---|---|---|
| 2,227,876 | 1/1941 | Bolt . |
| 3,239,417 | 3/1966 | Di Tullio et al. . |
| 3,264,301 | 8/1966 | Doorenbos et al. . |
| 3,285,918 | 11/1966 | Doorenbos et al. . |

FOREIGN PATENT DOCUMENTS

| | | |
|---|---|---|
| 775919 | 12/1971 | Belgium . |
| 970692 | 7/1975 | Canada . |
| 4949 | 10/1979 | European Pat. Off. . |
| 1465544 | 11/1965 | France . |

OTHER PUBLICATIONS

Neri et al., Endo., vol. 91, No. 2, pp. 427–437, (1972).
Doorenbos & Brown, J. Phar. Sci., 60, 8, pp. 1234–1235, (1971).
Doorenbos & Solomons, J. Phar. Sci., 62, 4, pp. 638–640, (1973).
Nayfeh et al., Steroids, 14, pp. 269–283, (1969).

Primary Examiner—Paul M. Coughlan, Jr.
Attorney, Agent, or Firm—Thomas E. Arther; Mario A. Monaco

[57] ABSTRACT

4-Aza-17β-substituted-5α-androstan-3-ones and their A-homo analogs of the formula:

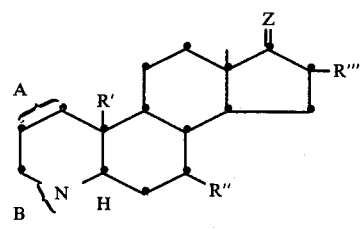

(I)

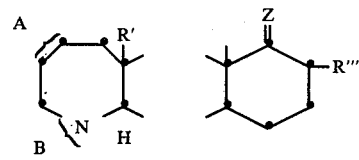

(II)     (III)

where Formula (I) may also have the structure of partial Formulas (II) and/or (III);

and pharmaceutically acceptable salts of the above compounds are active as testosterone 5α-reductase inhibitors, and thus useful topically for treatment of acne, seborrhea, female hirsutism, and systemically in treatment of benign prostatic hypertrophy.

19 Claims, No Drawings

4-AZA-17β-SUBSTITUTED-5α-ANDROSTAN-3-ONE-REDUCTASE INHIBITORS

This is a continuation-in-part of application, Ser. No. 020,371 filed March 15, 1979, and now abandoned, which, in turn, is a continuation-in-part of application Ser. No. 896,118 filed Apr. 13, 1978 and now abandoned.

BACKGROUND OF THE INVENTION

1. Field of the Invention

The present invention is concerned with novel 4-aza-17-substituted-5α-androstan-3-ones and their A- and D-homo analogs, and the use of these compounds as testosterone 5α-reductase inhibitors.

2. Description of the Prior Art

It is well known in the art that certain undesirable physiological manifestations, such as acne vulgaris, seborrhea, female hirsutism, and male pattern baldness and benign prostatic hypertrophy, are the result of hyperandrogenic stimulation caused by an excessive accumulation of testosterone or similar androgenic hormones in the metabolic system. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethylisobutyranilide. See Neri et al., *Endo.*, Vol. 91, No. 2 (1972). However, these products, though devoid of hormonal effects, are peripherally active, competing with the natural androgens for receptor sites, and hence have a tendency to feminize a male host or the male fetus of a female host.

It more recently became known in the art that the principal mediator of androgenic activity in some target organs is 5α-dihydrotestosterone, and that it is formed locally in the target organ by the action of testosterone-5α-reductase. It therefore has been postulated and demonstrated that inhibitors of testosterone-5α-reductase will serve to prevent or lessen symptoms of hyperandrogenic stimulation. Nayfeh et al., *Steroids*, 14, 269 (1969) demonstrated in vitro that methyl 4-androsten-3-one-17β-carboxylate was a testosterone-5α-reductase inhibitor. Then Voigt and Hsia, *Endocrinology*, 92, 1216 (1973), Canadian Pat. No. 970,692, demonstrated that the above ester and the parent free acid, 4-androsten-3-one-17β-carboxylic acid are both active inhibitors of testosterone-5α-reductase in vitro. They further demonstrated that topical application of either testosterone or 5α-dihydrotestosterone caused enlargement of the female hamster flank organ, or androgen dependent sebaceous structure. However, concommitant administration of 4-androsten-3-one-17β-carboxylic acid or its methyl ester inhibited the response elicited by testosterone but did not inhibit the response elicited by 5α-dihydrotestosterone. These results were interpreted as indicating that the compounds were antiandrogenic by virtue of their ability to inhibit testosterone-5α-reductase.

The novel compounds of the present invention are, therefore, potent antiandrogens by virtue of their ability to specifically inhibit testosterone-5α-reductase.

Heretofore, it has not been known to use 4-aza-17-substituted-5α-androstan-3-ones for treating hyperandrogenic conditions, although Selye, in Belgian Pat. No. 775,919, describes such a compound, and a number of other compounds, additionally having one or more carbonitrile substituents, as a catatoxic agent useful in the treatment of, among other conditions, prostatic hypertrophy.

A number of 4-aza steroid compounds are known. See, for example, U.S. Pat. Nos. 2,227,876; 3,239,417; 3,264,301; and 3,285,918; French Pat. No. 1,465,544; Doorenbos and Solomons, *J. Pharm. Sci.* 62, 4, pp. 638-640 (1973); Doorenbos and Brown, *J. Pharm. Sci.*, 60 8, pp. 1234-1235 (1971); and Doorenbos and Kim, *J. Pharm. Sci.* 63, 4, pp. 620-622 (1974). However, none of the known compounds suggest the 4-aza compounds of the present invention or their use in treating hyperandrogenic conditions.

SUMMARY OF THE INVENTION

The present invention is concerned with novel antiandrogenic 4-aza-17β-substituted-5α-androstan-3-ones, their A-homo analogs, certain isosteres and derivatives thereof, processes for their preparation, pharmaceutical formulations comprising the novel compounds as active ingredient, and methods of inhibiting 5α-reductase and of treating hyperandrogenic conditions with the novel compounds or their pharmaceutical formulations.

The present invention is particularly concerned with novel compounds of the formula:

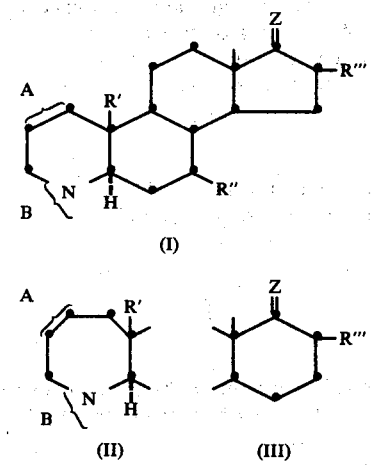

where Formula (I) may also have the structure of partial Formulas (II) and/or (III); wherein, A is (1)—CH$_2$—CH$_2$—;

(2)—CH=CH—;

(3)

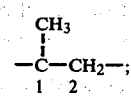

(4)

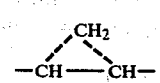

B is (1)

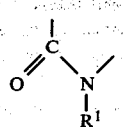

where
R$^1$ is
(a) hydrogen;
(b) methyl or ethyl;
(c) ethenyl;
(d) ethynyl;
(e) NR$^2$R$^3$ where R$^2$ and R$^3$ are hydrogen or methyl; or
(f) cyano; or (2)

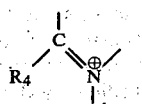

where X$^\ominus$ is any anion and R$^4$ is,
(a) OR$^5$ where R$^5$ is C$_{1-4}$ alkyl; or
(b) NR$^6$R$^7$, where R$^6$ and R$^7$ are hydrogen, methyl, ethyl, hydroxyl, or one of them may be absent, in which case the nitrogen atom is joined to an uncharged A-ring by a double bond;
R' is hydrogen or methyl;
R" is hydrogen or β-methyl;
R''' is β-methyl or hydroxyl;
Z is
(1) oxo;
(2) β-hydrogen and α-hydroxyl;
(3) α-hydrogen or α-hydroxyl and
(a)

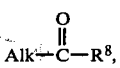

where Alk is present or absent and is a straight or branched hydrocarbon chain of 1 to 12 carbon atoms; and R$^8$ is,
(i) hydrogen,
(ii) hydroxyl,
(iii) C$_{1-4}$ alkyl
(iv) NR$^9$R$^{10}$, where R$^9$ and R$^{10}$ are each independently selected from hydrogen, C$_{1-4}$ straight or branched chain alkyl, C$_{3-6}$ cycloalkyl, phenyl; or R$^9$ and R$^{10}$ taken together with the nitrogen to which they are attached represent a 5-6 membered saturated ring comprising up to one other heteroatom selected from oxygen and nitrogen; or
(v) OR$^{11}$, where R$^{11}$ is M, where M is hydrogen or alkali metal, or C$_{1-18}$ straight or branched chain alkyl; benzyl; or
(b) Alk-OR$^{12}$, where Alk is always present and has the same meaning as above; and
R$^{12}$ is
(i) phenyl C$_{1-6}$ alkylcarbonyl,
(ii) C$_{5-10}$ cycloalkylcarbonyl,
(iii) benzoyl, or
(iv) C$_{1-18}$ alkoxycarbonyl;
(v) amino, or C$_{1-8}$ alkyl substituted amino, carbonyl; or
(vi) hydrogen, provided that Alk is a branched C$_3$-C$_8$ chain;

(4)

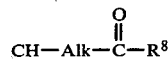

or CH-Alk-OR$^{12}$, where Alk is present or absent and has the same meaning as above, and R$^8$ and R$^{12}$ have the same meaning as above, and R$^{12}$ is also hydrogen or C$_{1-20}$ alkylcarbonyl;

(5)

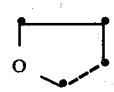

where the dashed bond replaces the 17α hydrogen;
(6) α-hydrogen and

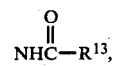

where R$^{13}$ is,
(a) C$_{1-12}$ alkyl; or
(b) NR$^9$R$^{10}$;
(7) α-hydrogen and cyano; or
(8) α-hydrogen and tetrazolyl;
and pharmaceutically acceptable salts of the above compounds.

Unless otherwise indicated, both the α and β stereo configurations for various substituents are intended.

The anion, X$^\ominus$, for the A-ring quaternary nitrogen compounds described above, may be any suitable, pharmaceutically acceptable anion, for example, those described below with regard to pharmaceutically acceptable salts.

The compounds of Formulas I, II, and III can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecysulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

A preferred embodiment of the novel compounds is that with structural formula:

with an appropriate amine to form a 4-substituted-4-aza-5-androsten-3-one compound; and (3) reacting the 4-aza-5-androsten-3-one with hydrogen under catalytic conditions to form a 4-aza-5α-androstan-3-one compound of Formula I. The above reactions are schematically represented in the following diagram;

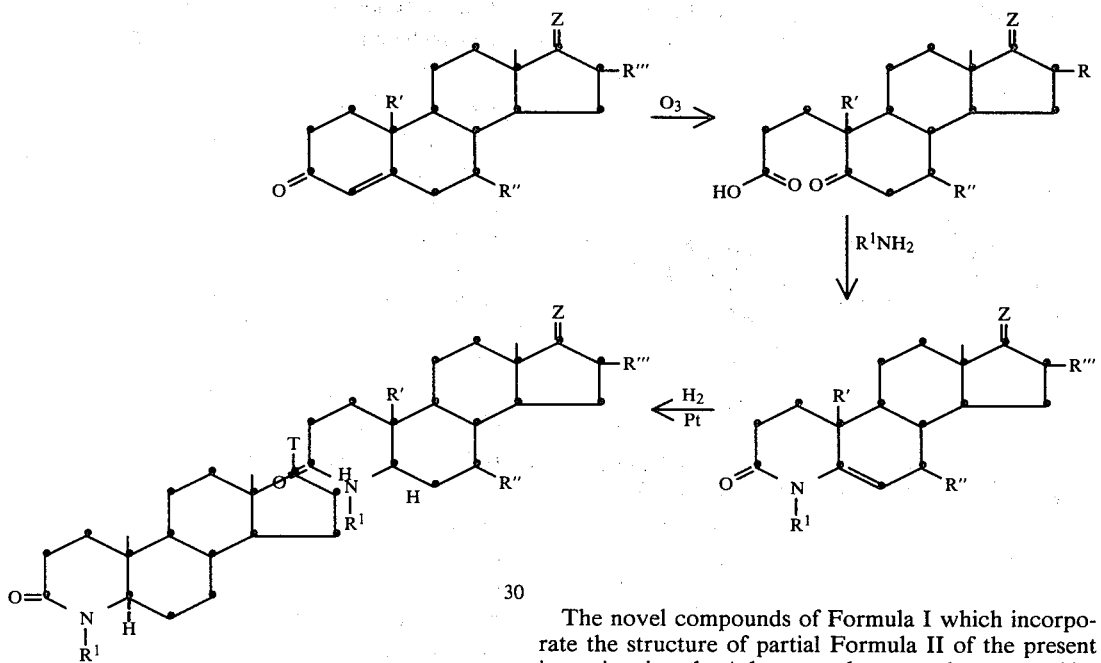

wherein R¹ hydrogen, methyl, or amino; and T is CONHCH₂CH₃,

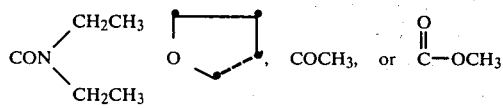

A still more preferred embodiment of the novel compounds is that wherein R¹ is methyl, and T is CONHCH₂CH₃ or CON(CH₂CH₃)₂.

Representative compounds of the present invention are, among others, the following:

17β-N,N-diethylcarbamoyl-4-methyl-4-aza-5α-androstan-3-one
17β-N,N-diethylcarbamoyl-4-aza-5α-androstan-3-one
17β-N,N-diethylcarbamoyl-4-amino-4-aza-5α-androstan-3-one
4-aza-5α-20-spiroxan-3-one
4-methyl-4-aza-5α-20-spiroxan-3-one
17β-N-ethylcarbamoyl-4-methyl-4-aza-5α-androst-3-one
4-methyl-4-aza-5α-pregnane-3,20-dione
4-ethyl-4-aza-5α-20-spiroxan-3-one
17β-carbomethoxy-4-methyl-4-aza-5α-androstan-3-one The novel compounds of Formula I of the present invention may be prepared by a method comprising the steps of (1) treating a 4-androstene-3-one derivative with an oxidizing agent such as ozone at reduced temperatures of about −70° to −80° C. to form a 5-oxo-3,5-secoandrostan-3-oic acid compound; (2) reacting the secoandrostanoic acid compound product of step (1)

The novel compounds of Formula I which incorporate the structure of partial Formula II of the present invention, i.e., the A-homo analogs, may be prepared by a method comprising the steps of (1) reacting testosterone with ethanedithiol in the presence of boron trifluoride etherate to form a 3-dithioketal derivative of the testosterone; (2) reacting the product of step (1) with sodium and liquid ammonia to remove the 3-dithioketal substituent; (3) reacting the product of step (2) with dihydropyran in the presence of p-toluene-sulfonyl chloride to form a 17-tetrahydropyranyloxy derivative; (4) reacting the product of step (3) with borane and then with sodium hydroxide and hydrogen peroxide to form a 4-hydroxy-5α-hydrogen compound; (5) reacting the product of step (4) with chromium trioxide to form a 4-keto compound; (6) treating the product of step (5) with acid to remove the 17-tetrahydropyranyl protective group and form a 17-hydroxy compound; (7) reacting the product of step (6) with benzoyl chloride to form a 17-benzoate; (8) reacting the product of step (7) with hydroxylamine hydrochloride to form a 4-oxime compound; and (9) reacting the product of Step (8) with thionyl chloride and then potassium hydroxide to form a compound of Formula II, an A-homo-4α-aza compound.

The above reactions are schematically represented in the following diagram:

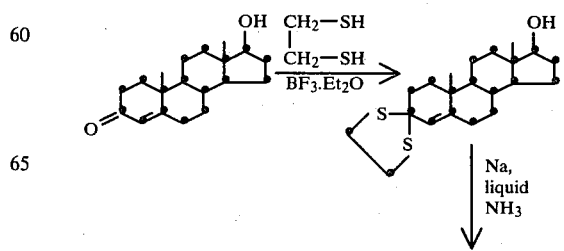

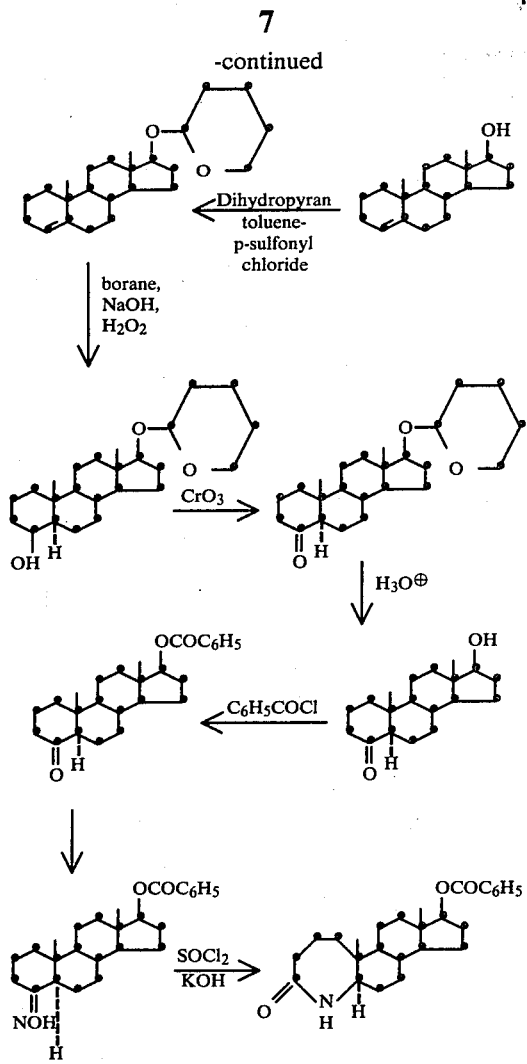

The novel compounds of Formula I which incorporate the structure of partial Formula III of the present invention, i.e., the D-homo analogs, may be prepared by a number of different methods known in the art, including those described in *J. Steroid Biochem.*, Vol. 5, No. 4, p. 298 (June 1974) by Alig et al. and Kerb et al., and in *Helv. Chim Acta*, Vol. 23, pp. 376–384 and 840–845 by Goldberg and Mannier.

Novel compounds of the present invention having a 1,2α-methylene substituent, i.e. where A is

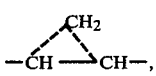

may be prepared in accordance with methods known in the art, including, e.g., that described in *Chem. and Ind.*, p. 1710 (Oct. 10, 1964) by Loev et al.

Novel compounds of the present invention which are Δ1, i.e. where A is —CH=CH—, and in which the 4-nitrogen carries a substituent other than hydrogen, may be prepared in accordance with the procedures described in Example 15 which follows. Where the 4-nitrogen is substituted only with hydrogen, the novel compounds of the present invention may be prepared in accordance with the procedures described in Example 16 following.

A preferred process for preparing 17β-N,N-diethylcarbamoyl-4-methyl-4-aza-5α-androstan-3-one, an especially preferred compound of the present invention, comprises the following steps: (a) pregnenolone (V), an available starting material, is treated by the haloform King reaction with iodine and pyridine to form the 20-pyridinum iodide derivative of the pregnenolone (VI); (b) the pyridinium iodide derivative (VI) is hydrolyzed to the methyl ester of 17-carboxy pregnenolone (VII) with sodium methoxide and methanol, the ester form being preferred for carrying out the following Oppenhauer reaction; (c) the methyl ester of 17-carboxy pregnenolone (VII) is treated with aluminum isopropoxide and cyclohexanone in an appropriate solvent such as toluene to yield methyl-4-androstene-3-one-17-carboxylate (VIII) (d) the methyl-4-androstene-3-one-17-carboxylate (VIII) thus formed is hydrolyzed to the 17-acid (IX) under acid conditions in a methanol: water solvent of approximately 4:1 proportions; (e) the 17 acid (IX) is then treated with an oxalyl chloride: pyridine complex of approximately 1:1 proportions in toluene or other suitable solvent, e.g. xylene, to form the 17-acid chloride (X); (f) the 17-acid chloride (X) is then treated in situ with an excess of diethylamine to form the 17β-N,N-diethylcarbamoyl-4-androstene-3-one (XI); (g) the 4-androstene-3-one (XI) thus formed is oxidized by treatment with sodium periodate and potassium permanganate, using tert-butanol and water as a solvent system, to the corresponding 5-oxo-3,5-secoandrostan-3-oic acid (XII); (h) the secoandrostanoic acid (XII) is then converted to the corresponding 4-aza compound (XIII) by treating it with methylamine in ethylene glycol for a period of about 1 hour over which time the reaction mixture temperature is raised to from 140°–180° C. where it is maintained from 0.5 to 5 minutes; (i) the resulting 17β-N,N-diethylcarbamoyl-4-methyl-4-aza-5-androsten-3-one (XIII) is then hydrogenated by treating it with hydrogen at room temperature to 60° C. or higher, using platinum oxide as the catalyst, to form the 17β-N,N-diethylcarbamoyl-4-methyl-4-aza-5α-androstan-3-one (XIV) final product, which is then separated and purified.

The above reactions are schematically represented in the following diagram:

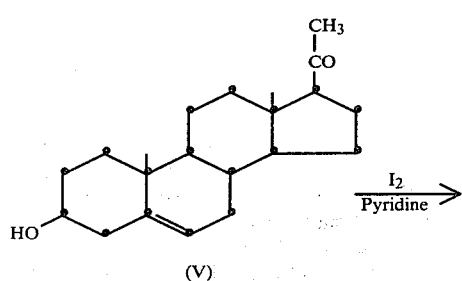

(V)

-continued

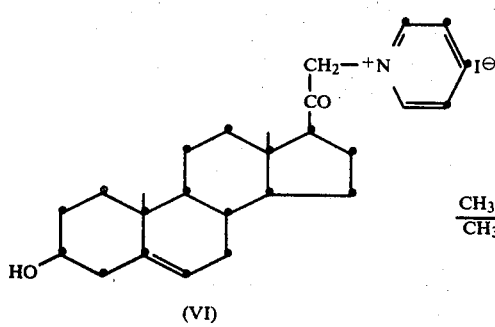

(VI)

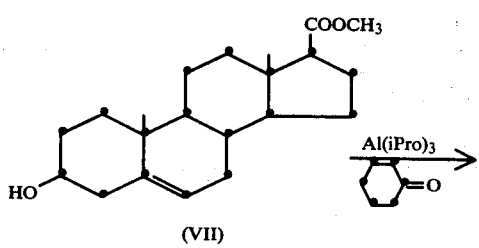

(VII)

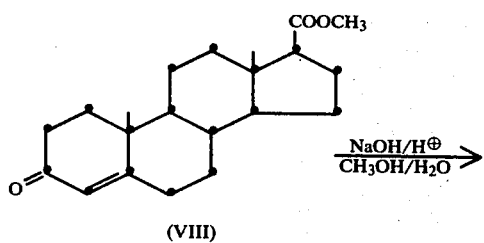

(VIII)

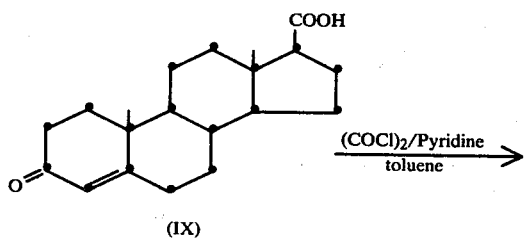

(IX)

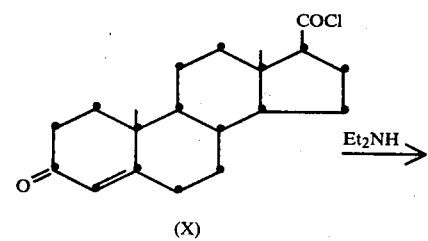

(X)

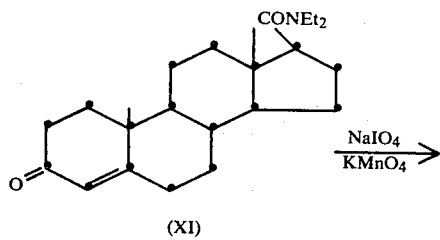

(XI)

-continued

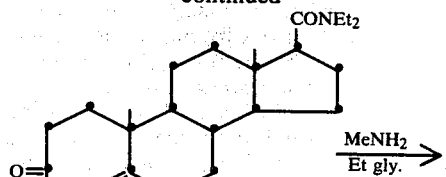

(XII)

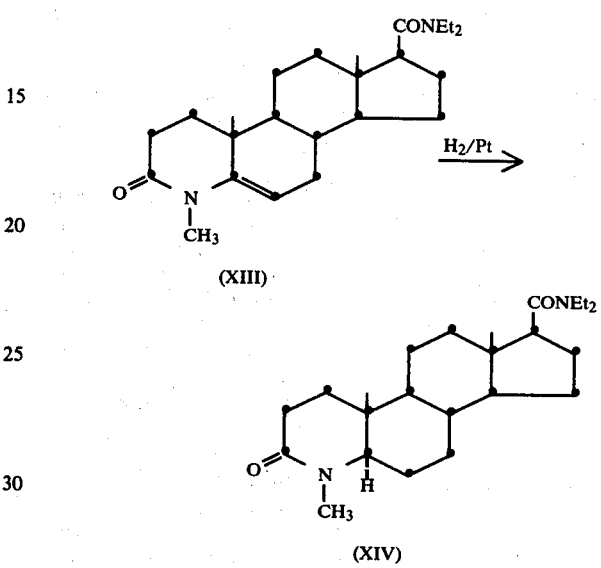

(XIII)

(XIV)

The compounds of the present invention, prepared in accordance with the method described above, are, as already described, potent antiandrogens by virtue of their ability to specifically inhibit testosterone-5α-reductase.

Accordingly, the present invention is particularly concerned with providing a method of treating the hyperandrogenic conditions of acne vulgaris, seborrhea, and female hirsutism by topical administration, and a method of treating all of the above conditions as well as benign prostatic hypertrophy, by parenteral administration, of the novel compounds of the present invention.

The present invention is thus also concerned with providing suitable topical and parenteral pharmaceutical formulations for use in the novel methods of treatment of the present invention.

The compositions containing the compounds of the present invention as the active ingredient for use in the treatment of benign prostatic hypertrophy can be administered in a wide variety of therapeutic dosage forms in conventional vehicles for systemic administration, as, for example, by oral administration in the form of tablets, capsules, solutions, or suspensions, of by intravenous injection. The daily dosage of the products may be varied over a wide range varying from 50 to 2,000 mg. The compositions are preferably provided in the form of scored tablets containing 5, 10, 25, 50, 100, 150, 250, and 500 milligrams of the active ingredient for the symptomatic adjustment of the dosage to the patient to be treated. An effective amount of the drug is ordinarily supplied at a dosage level of from about 1 mg. to about 50 mg./kg. of body weight per day. Preferably the range is from about 1 mg. to 7 mg./kgs. of body weight per day. These dosages are well below the toxic dose of the product. Capsules containing the product of this invention can be prepared by mixing an active compound of the present invention with lactose and magnesium stearate, calcium stearate, starch, talc, or other carriers, and placing the mixture in gelatin capsule. Tablets may be prepared by mixing the active ingredient with conventional tableting ingredients such as calcium phosphate, lactose, corn starch or magnesium stearate. The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration sterile suspensions and solutions are desired. Isotonic preparations which generally contain suitable preservative are employed when intravenous administration is desired.

For the treatment of acne vulgaris, seborrhea, female hirsutism, the compounds of the present invention are administered in the formula of pharmaceutical composition comprising the active compound in combination with a pharmacologically acceptable carrier adapted for topical administration. These topical pharmaceutical compositions may be in the form of a cream, ointment, gel or aerosol formulation adapted for application to the skin. These topical pharmaceutical compositions containing the compounds of the present invention ordinarily include about 0.1% to 15%, preferably about 5%, of the active compound, in admixture with about 95% of vehicle.

The method of preparing the novel compounds of the present invention, already described above in general terms, may be further illustrated by the following examples:

EXAMPLE 1

17β-N,N-diethylcarbamoyl-4-methyl-4-aza-5α-androstan-3-one

A. 3-oxo-N,N-diethyl-4-etienamide

Twenty grams of sodium 3-oxo-4-etienate was suspended in 360 ml. of dry benzene and 0.13 ml. of pyridine and cooled to 14° C. The suspension was treated with 20 ml. of oxalyl chloride and stirred at 15° C. for 15-20 min. The suspension was evaporated to dryness and then slurried up, as a suspension, in 125 ml. of dry tetrahydrofuran. This suspension was then added to a solution of 25 ml. of diethylamine in 125 ml. of tetrahydrofuran and stirred at room temperature for 1 hr., after which the mixture was poured into 4 l. of ice water. A semi-crystalline precipitate resulted which was extracted with ethyl acetate, washed with water and then saturated brine, and dried and evaporated to 25.7 g. of product. The product was recrystallized from ethyl ether; the first crop of 10.0 g. had a m.p. of 127°-129° C. and the second crop of 3.1 g. had a m.p. of 114°-119° C.

B. 17β-N,N-diethylcarbamoyl-5-oxo-3,5-secoandrostan-3-oic acid

Fifteen grams of the product of Step A. was dissolved in 150 ml. of dichloromethane and 75 ml. of methanol and cooled to −78° C., after which ozone was bubbled through the solution until a blue color persisted. The reaction solution was then warmed to room temperature and purged with nitrogen, after which it was evaporated to dryness at 35° C. The residue was dissolved in benzene and extracted three times with 2.5 N NaOH. These basic washes were combined and acidified with concentrated HCl, extracted with benzene, washed, dried, and evaporated to 11.5 g. of a white crystalline solid. The product was recrystallized from ethyl acetate and found to have a m.p. of 205°-208° C.

C. 17β-N,N-diethylcarbamoyl-4-aza-4-methyl-5-androsten-3one

To 190 ml. of ethanol was added 26.3 g. of the product of Step B to form a solution. The solution was cooled in an ice bath and saturated with methylamine, and then heated at 180° C. for 8 hrs. The reaction mixture was then cooled to room temperature and evaporated to yield 22.3 g. of a yellowish solid. After chromatographing and recrystallization from ethyl ether, the final product was found to have a m.p. of 120°-122° C.

D. 17β-N,N-diethylcarbamoyl-4-methyl-4-aza-5α-androstan-3-one

To 1 liter of glacial acetic acid was added 36.5 g. of the product of Step C to form a solution. The solution was then treated with 3.5 g. of platinum oxide catalyst and hydrogenated at 40 p.s.i. at room temperature for 8 hrs. The reaction mixture was then filtered and evaporated to dryness. The residue was dissolved in chloroform and washed with a bicarbonate solution, brine, and then dried and evaporated to dryness. The product was recrystallized from ethyl ether to yield 30.65 g. of a white crystalline final product having a m.p. of 168°-170° C.

EXAMPLES 2-27

Following the procedures described in Example 1 above, but substituting for the 3-oxo-4-etienate in Step A an equimolar amount of other available or readily prepared 3-oxo-Δ⁴ compounds, or substituting for the diethylamine an equimolar amount of another appropriate amine, there were prepared the compounds of Formula I of the present invention enumerated in the following table.

TABLE

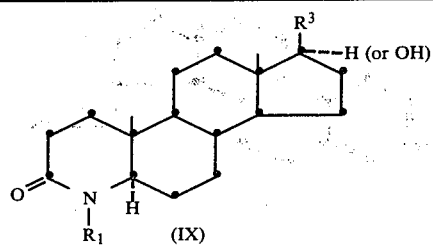

(IX)

| Example No. | 17α | $R^1$ | $R^3$ | R″ | m.p. (°C.) |
|---|---|---|---|---|---|
| 2 | H | H | $CON(CH_2CH_3)_2$ | H | 263-265 |
| 3 | — | H | 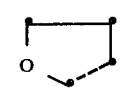 | H | 283-285 |

TABLE-continued

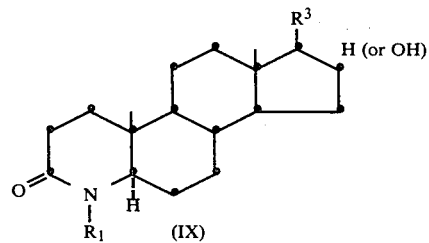

(IX)

| Example No. | 17α | R¹ | R³ | R" | m.p. (°C.) |
|---|---|---|---|---|---|
| 4 | — | CH₃ | (furan-2-yl, O in ring) | H | 138-140 |
| 5 | H | H | COCH₃ | H | 272-275 |
| 6 | H | CH₃ | COCH₃ | H | 218-220 |
| 7 | H | CH₃ | CONHCH₂CH₃ | H | 249-251 |
| 8 | H | H | COOCH₃ | H | 300-302 |
| 9 | H | CH₃ | NHCOCH₃ | H | 284-287 |
| 10 | H | CH₃ | CH₃<br>\|<br>CHCOOCH₃ | H | 162-165 |
| 11 | H | CH₃ | CH₃<br>\|<br>CHCOOH | H | 307-309 |
| 12 | H | CH₃ | CONH₂ | H | 246-248 |
| 13 | H | CH₃ | CONH(CH₂)₇CH₃ | H | glass (mass spectra M⁺ 444) |
| 14 | H | CH₃ | CON(CH₃)₂ | H | 240-242 |
| 15 | H | CH₃ | CH₃<br>\|<br>CON(CH)₂<br>\|<br>CH₃ | H | 181-183 |
| 16 | H | CH₃ | COOH | H | >300 |
| 17 | H | CH₃ | COOCH₃ | H | 133-135 |
| 18 | H | CH₃ | CH₃<br>\|<br>CH(CH₂)₂CON(C₂H₅)₂ | H | 165-167 |
| 19 | H | CH₃ | CH₃<br>\|<br>CH(CH₂)₂COOH | H | 256-258 |
| 20 | H | CH₃ | CH₃<br>\|<br>CHCON(C₂H₅)₂ | H | 216-218 |
| 21 | H | CH₃ | CH₃<br>\|<br>CH(CH₂)₂COOCH₃ | H | 95-97 |
| 22 | N | NHCH₃ | CON(C₂H₅)₂ | H | 227-229 |
| 23 | H | CH₃ | CH₂CON(C₂H₅)₂ | H | 159-162 |
| 24 | H | CH₃ | CH₂COO(C₂H₅) | H | 55-57 |
| 25 | — | CH₂CH₃ | (furan-2-yl, O in ring) | H | glass |
| 26 | — | CH₃ | (furan-2-yl, O in ring) | CH₃ | 115-119 |
| 27 | OH | CH₃ | CH₃<br>\|<br>CH—OH | H | 210-216 |
| 28 | H | CH₃ | CH₃<br>\|<br>CHCH₂OH | H | 194-197 |

EXAMPLE 28

17β-benzoyloxy-4a-aza-5α-A-homoandrostan-4-one

A. 17β-hydroxy-4-androstene-3-thioketal

A solution is prepared from 7.5 g of testosterone, 37.5 ml of glacial acetic acid, 4.5 ml of ethanedithiol, and 3.0 ml of boran trifluoride etherate at 0° C. The mixture is allowed to come to room temperature where it is maintained for 1.5 hrs. The mixture is then diluted with water, extracted with chloroform, and washed with 5% sodium bicarbonate, then water several times, then a saturated sodium chloride solution. The mixture is then dried and evaporated to yield a white solid which is recrystallized from methanol to give 9.0 g of final product (95% yield) having a m.p. of 160°-162° C.

B. 17β-hydroxy-4-androstene

To 60 ml of anhydrous liquid ammonia is added 1.2 g of metallic sodium. To this solution is added 1.0 g of the thioketal in 10 ml of dry tetrahydrofuran and the solution is refluxed for 20 min. The solution is quenched with a few ml of ethanol and evaporated at room temperature. The solution is then diluted with water, extracted with dichloromethane, washed with water, HCl, then water, and dried and evaporated to a white solid having a m.p. of 149°-152° C. (609 mg, 81% yield).

C. 17β-tetrahydropyranyloxy-4-androstene

To 30 ml of dihydropyran containing 450 mg of p-toluenesulfonyl chloride is added 6.0 g of the product of Step B and the solution is stirred at room temperature for 1 hour. The solution is the diluted with ethyl ether and washed with a 20% pyridine water mixture twice, and then water, then brine, and dried and evaporated to yield a pale yellow oil which crystallizes (8.5 g), and has a m.p. of 92°-96° C.

D. 17-β-tetrahydropyranyloxy-4β-hydroxy-5α-androstane

To a cooled solution (0° C.) of 5 ml of 1M borane in tetrahydrofuran in 2.7 ml of dry tetrahydrofuran is added 500 mg. (1.4 millimole) of the product of Step C. in 2.0 ml of dry tetrahydrofuran. The clear solution is stirred for 1 hr. at room temperature and then cooled to 0° C. and treated with 5 ml of 2.5 N sodium hydroxide followed by 4 ml of 30% hydrogen peroxide. The solution is stirred for 1 hr. at room temperature, diluted with water and extracted with ethyl ether, washed with water, brine, dried and evaporated to an oily crystalline material. The product is washed with cold methanol and pumped dry to give 175 mg of final product having a m.p. of 167°-170° C.

E. 17$\beta$-tetrahydropyranyloxy-5$\alpha$-androstan-4-one

To 0.42 ml of dry pyridine and 6.3 ml of dry dichloromethane is slowly added 0.264 g of chromium trioxide and the mixture is stirred for 15 min. at room temperature. To the mixture is added a solution of 175 mg of the product of Step D in 0.7 ml of dichloromethane and the resulting mixture is stirred for 20 min. at room temperature. The mixture is diluted with water, extracted with ethyl ether, and washed with 2.5 N sodium hydroxide, water, and brine. The mixture is then dried and evaporated to a clear oil.

F. 17$\beta$-hydroxy-5$\alpha$-androstan-4-one

To 75 ml of ethanol is added 2.32 g of the product of Step E to form a solution which is then treated with 5 ml of 2.5 N hydrochloric acid and warmed on a steam bath for 40 min. to yield 2.1 g of a crystalline product having a m.p. of 123°-126° C.

G. 17$\beta$-benzoyloxy-5$\alpha$-androstan-4-one

To 12 ml of dry pyridine and 6 ml of benzoyl chloride is added 2.0 g of the product of Step F to form a solution which is heated on a steam bath for 30 min. and then poured into 175 ml of ice water and stirred to decompose the excess chloride. The reaction mixture is filtered, washed with water, and pumped dry under high vacuum at 50° C. to yield 1.7 g of final product.

H. 17$\beta$-benzoyloxy-5$\alpha$-androstan-4-oxime

To 125 ml of ethanol and 30 ml of dry pyridine is added 2.0 g of the product of Step G to form a solution which is treated with 420 mg of hydroxylamine hydrochloride and stirred at room temperature. The reaction mixture is chromatographed by thin layer chromatography on slica gel in 20% ethylacetate/benzene which is allowed to run overnight. The product is concentrated to low volume at 30°-40° C. under high vacuum and diluted slowly with water to form a white crystalline material which is filtered, washed with water, dissolved in ethyl ether, dried, and recrystallized from ethyl ether.

I. 17$\beta$-benzoyloxy-4a-aza-5$\alpha$-A-homoandrostan-4-one

To 3.3 ml of distilled thionyl chloride at $-78°$ C. is added 500 mg of the product of Step H and the resulting solution is stirred for 1-2 min. and then slowly added to 50 ml of 4 N potassium hydroxide at 20° C. A solid precipitate forms which is filtered and washed well with water and then ethyl ether. The product is recrystallized from ethylacetate, washed with ethylacetate, ethyl ether and dried to yield 210 mg of final product.

EXAMPLE 29

17$\beta$-N,N-dibutylcarbamoyl-4-methyl-4-aza-5$\alpha$-androst-1-en-3-one

A solution of 0.20 g. of anhydrous diisopropylamine in 5.0 ml. of anhydrous tetrahydrofuran is treated at $-78°$ C. under nitrogen with 0.9 ml. of 2.2 M butyllithium. After 20 minutes at $-78°$ C., a solution of 388 mg. of 17$\beta$-N, N-dibutylcarbamoyl-4-methyl-4-aza-5$\alpha$-androstan-3-one in 3 ml. of tetrahydrofuran is added dropwise to the reaction mixture. After stirring at $-78°$ C. for 30 minutes, a solution of 440 mg. of phenyl disulfide in 1 ml. of tetrahydrofuran is added slowly to the reaction mixture. After stirring for 10 minutes at 78° C., the reaction mixture is allowed to warm to room temperature. The mixture is then added to water, and the product is extracted into ethyl acetate. The organic layer is washed with dilute sodium hydroxide solution, then water, then dilute hydrochloric acid, and finally with saturated sodium chloride solution. The solution is dried over calcium sulfate and is then concentrated to the crude solid product. Elution through 30 g. of silica gel with increasing amounts of ethyl acetate in hexane affords the 2-phenylthio derivative as an apparent mixture of two isomers. This material, suspended in 5 ml. of 20% aqueous methanol is treated with a solution of 225 mg. of sodium metaperiodate in 2 ml. of water. After stirring 16 hours, the reaction mixture is diluted with water and extracted with methylene chloride. The organic layer is washed with water, dried, and concentrated to leave the crude sulfoxide. A solution of this material in 5 ml. of toluene is refluxed for 30 minutes. The solvent is removed and the residue is chromatographed on 20 g. of silica gel eluting with increasing amounts of ethyl acetate in ether. The final product crystallized on trituration with ether.

EXAMPLE 30

A solution of 291 mg of 17$\beta$-N,N-diethylcarbamoyl-4-aza-5$\alpha$-androstan-3-one in 3 ml of methylene chloride is added at 0° C. to a solution of 117 mg of trimethyloxonium fluoroborate in methylene chloride. The mixture is then stirred at 0° C. for 6 hours and then is treated with 125 mg of 1,5 diazobicyclo [5,4,0] undec-5-ene. Stirring in continued for 2 hours and the reaction mixture is diluted with anhydrous ether. The organic solution is separated from the residue and concentrated under reduced pressure to leave the crude lactam ether. This material is then converted to the corresponding $\Delta$1 compound in accordance with the procedures described above in Example 29.

EXAMPLE 31

17$\beta$-N,N-diethylcarbamoyl-3-methimino-4-methyl-4-aza-5$\alpha$-androstane

A mixture of 195 mg of 17$\beta$-N,N-dimethylcarbamoyl-4-methyl-4-aza-5$\alpha$-androstan-3-one and 70 mg of dimethylsulfate in 1.0 ml of chloroform was heated under nitrogen in a bath kept at 75° C. The mixture was heated overnight and then the condenser was removed and the chloroform was allowed to distill away. The resulting gum (under a nitrogen stream) was heated at 75° C. for 3 hours and then cooled and pumped free of solvent under reduced pressure (5 mm Hg, room temperature). The product was tacky and appeared to be hygroscopic. It was dissolved in 3 ml of anhydrous methanol and brought to reflux while methylamine gas was bubbled into the mixture. This treatment was continued for 3 hours, after which the methylamine was removed by distillation with methanol, and the mixture was then concentrated to a thick, tacky residue. A 1:1 mixture of ethyl acetate:ether (6 ml) was added to the material and triturated until completely solid. The layers were separated by centrifugation and the solid was rinsed with ether. The solid was dried in vacuo and then was washed with water twice with 4 ml. The remaining solid was dried and crystallized from ethyl acetate to leave 62 mg of product having a m.p. of 184°-187° C. On recrystallization the m.p. was 183°-186° C.

EXAMPLE 32

4-Methyl-3-oxo-4-aza-5α-pregn-17(20)-ene-21-oic acid

A. 4-Methyl-4-aza-5α-androstan-3,17-dione

A 1.5 g sample of 17-hydroxy-4-methyl-4-aza-5α-androstan-3-one was partially dissolved in 75 ml of acetone, stirred vigorously, and treated with 3.6 ml of 8 N Jones Reagent. The mixture was stirred at room temperature for 15 min. and then quenched with several drops of methanol. The mixture was filtered through silica and evaporated to dryness. The residue was dissolved in chloroform and passed through a short bed of silica gel. The product was chromatographed and recrystallized from ether to yield 806 mg.

B. Ethyl-4-methyl-3-oxo-4-aza-5α-pregn-17(20)-ene-21-oate

An 800 mg sample (2.64 mmole) of the product of Step A above was suspended in 1.46 ml (1.67 g, 7.92 mmole) of methyl diethylphosphonoacetate. There was then added dropwise to the suspension over 20 min. a solution of sodium ethoxide prepared from 190 mg of sodium in 3.3 ml of distilled ethanol. Addition took place at room temperature, after which the reaction was carried out at reflux. After 7 hours the starting material appeared to be gone. The reaction mixture was evaporated to dryness, diluted with water, acidified with acetic acid, extracted with ether, and washed with water, saturated bicarbonate, water and saturated brine. The reaction mixture was then dried and evaporated to produce spontaneous crystallization. The product was recrystallized from ether to yield 461 mg of white crystals, m.p. 150°-152° C.

C. 4-Methyl-3-oxo-4-aza-5α-pregn-17(20)-ene-21-oic acid

A 265 mg sample of the product of Step B above was dissolved in 10 ml of methanol and 1 ml of water, treated with 200 mg of potassium carbonate, and refluxed for 1 hour. Thin layer chromatography on silica gel in 1:1 ethyl acetate/acetone showed mostly starting material, and the reaction mixture was refluxed overnight. The reaction mixture was evaporated to a slurry, diluted with water, extracted with ethyl acetate, acidified, and filtered off to give a white precipitate, which was then dried to 206 mg, m.p. 285°-288° C. (dec.).

EXAMPLE 33

17β-N,N-diethylcarbamoyl-4-methyl-4-aza-5α-androst-1-en-3-one

At −78° C. a solution of 1.164 g of 17β-N,N-diethylcarbamoyl-4-methyl-4-aza-5α-androstan-3-one in 12 ml of tetrahydrofuran was treated with 6 ml of a solution of lithium diisopropylamide, and was then allowed to come to 0° C. The resulting solution was added at 0° C. to a solution of 900 mg of diphenyldisulfide in 5 ml of tetrahydrofuran over a period of 5 min. with stirring. The mixture was then allowed to stand at room temperature for 1.5 hr and was then treated with water. The mixture was extracted with ethyl acetate, and the organic layer was washed successively with 5% sodium hydroxide solution, water, 2.5 N hydrochloric acid solution, water, saturated sodium chloride solution, and finally dried over calcium sulfate and concentrated to leave 1.68 g of residue. This residue was triturated with 50 ml of hexane, cooled, and dissolved in about 8 ml of ethyl acetate. The residue solution was seeded with the phenylsulfide, and the resulting crystalline material was separated and washed with ether to yield 282 mg.

The combined mother liquors were prepared on 6×2000μ plates, eluting with 30% hexane/ethyl acetate. Two spots were isolated; the major spot (lower) was the desired product (crystalline) and when combined with the first product, gave 995 mg.

A solution of the monophenylthio-steroid (990 mg) in 15 ml of methanol was treated, with vigorous stirring, with a solution of 700 mg of sodium metaperiodate in 3 ml of water. The reaction mixture was stirred at room temperature overnight and was cloudy with a thick precipitate.

This crude sulfone (about 950 mg) was dissolved in 15 ml of toluene and was heated at reflux for 2 hours. It was diluted with ethyl acetate and was extracted with 5% sodium hydroxide solution, water and saturated sodium chloride solution. The reaction mixture was then dried and concentrated to a semi-crystalline mass which was recrystallized from ethyl acetate by addition of hexane to give 235 mg of the desired product, m.p. 202°-205° C. A portion was recrystallized from ethyl acetate to give and analytical sample, m.p. 200°-202° C.

EXAMPLE 34

(1) Tablets—10,000 scored tablets for oral use, each containing 500 mg. of active ingredient are prepared from the following ingredients:

|  | Gm. |
|---|---|
| 17β-N,N—diethylcarbamoyl-4-methyl-4-aza-5α-androstan-3-one | 5000 |
| Starch, U.S.P. | 350 |
| Talc, U.S.P. | 250 |
| Calcium stearate | 35 |

The active ingredient is granulated with a 4% w./v. aqueous solution of methylcellulose U.S.P. (1500 cps). To the dried granules is added a mixture of the remainder of the ingredients and the final mixture compressed into tablets of proper weight.

(2) Capsules—10,000 two-piece hard gelatin capsules for oral use, each containing 250 mg. of active ingredient are prepared from the following ingredients:

|  | Gm. |
|---|---|
| 17β-N,N—diethylcarbamoyl-4-methyl-4-aza-5α-androstan-3-one | 2500 |
| Lactose, U.S.P. | 1000 |
| Starch, U.S.P. | 300 |
| Talc, U.S.P. | 65 |
| Calcium Stearate | 25 |

The active ingredient is mixed with the starch lactose mixture followed by the talc and calcium stearate. The final mixture is then encapsulated in the usual manner. Capsules containing 10, 25, 50, and 100 mg. of active ingredient are also prepared by substituting 100, 250, 500, and 1000 gm. of 2500 gm. in the above formulation.

(3) Soft elastic capsules—One-piece soft elastic capsules for oral use, each containing 500 mg. of active material are prepared in the usual manner by first dispersing the active material in sufficient corn oil to render the material capsulatable.

(4) Aqueous suspension—An aqueous suspension for oral use containing in each 5 ml., 0.25 g. of active ingredient is prepared from the following ingredients:

|  | Gm. |
|---|---|
| 17β-N,N—diethylcarbamoyl-4-methyl-4-aza-5α-androstan-3-one | 500 |
| Methylparaben, U.S.P. | 7.5 |
| Propylparaben, U.S.P. | 2.5 |
| Saccharin sodium | 12.5 |
| Glycerin | 3000 |
| Tragacanth powder | 10 |
| Orange oil flavor | 10 |
| F.D. & C. orange dye | 7.5 |
| Deionized water, q.s. to 10,000 ml. | |

(5) Gel Formulation
0.1 mg. disodium edetate
1.30 mg. of purified $H_2O$
300 mg. isopropanol
26 mg. hydroxypropylcellulose
50 mg. 17β-N,N-diethyl-carbamoyl-4-methyl-4-aza-5α-androstan-3-one
q.s.a.d. 1 gm. propylene glycol (6) Ointment Formulation
50 mg. wool alcohols B.P.
150 mg. amichol C
350 mg. white wax
50 mg. 17β-N,N-diethyl-carbamoyl-4-methyl-4-aza-5α-androstan-3-one
q.s.a.d. 1 gm. isopropyl myristate

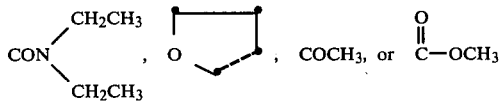

What is claimed is:
1. A compound of the formula:

(I)

(II)          (III)

where Formula (I) may also have the structure of partial Formulas (II) and/or (III); wherein, A is
(1) —$CH_2$—$CH_2$—;
(2) —CH=CH—;
(3)

$$-\underset{1}{\overset{CH_3}{\underset{|}{C}}}-\underset{2}{CH_2}-;$$

or
(4)

$$-CH\underset{\diagdown}{\overset{\diagup CH_2}{\phantom{X}}}CH-$$

B is
(1)

where
$R^1$ is,
(a) hydrogen;
(b) methyl or ethyl;
(c) ethenyl;
(d) ethynyl;
(e) $NR^2R^3$ where $R^2$ and $R^3$ are hydrogen or methyl; or
(f) cyano; or
(2)

where $X^\ominus$ is any anion and $R^4$ is,
(a) $OR^5$ where $R^5$ is $C_{1-4}$alkyl; or
(b) $NR^6R^7$, where $R^6$ and $R^7$ are hydrogen or methyl;

R' is hydrogen or methyl;
R" is hydrogen or β-methyl;
R''' is hydrogen, β-methyl or hydroxyl;
Z is
(1) α-hydrogen or α-hydroxyl and
(a)

$$Alk-\overset{O}{\underset{\|}{C}}-R^8,$$

where AlK is present or absent and is straight or branched hydrocarbon chain of 1 to 12 carbon atoms; and $R^8$ is,
(i) hydrogen,
(ii) hydroxyl,
(iii) $C_{1-4}$alkyl
(iv) $NR^9R^{10}$, where $R^9$ and $R^{10}$ are each independently selected from hydrogen, $C_{1-8}$ straight or branched chain alkyl, $C_{3-6}$ cycloalkyl, phenyl; or $R^9$ and $R^{10}$ taken together with the nitrogen to which they are attached represent a 5-6 membered saturated ring comprising up to one other heteroatom selected from oxygen and nitrogen; or
(v) $OR^{11}$, where $R^{11}$ is M, where M is hydrogen or alkali metal, or $C_{1-18}$ straight or branched chain alkyl; benzyl; or
(b) Alk-$OR^{12}$, where Alk is always present and has the same meaning as above, and $R^{12}$ is
(i) phenyl $C_{1-6}$ alkylcarbonyl,
(ii) $C_{5-10}$ cycloalkylcarbonyl, (iii) benzoyl, or
(iv) $C_{1-8}$ alkoxycarbonyl;
(v) amino, or $C_{1-8}$ alkyl substituted amino, carbonyl; or
(vi) hydrogen, provided that Alk is a branched $C_3$-$C_8$ chain;

(2)

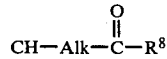

or CH-Alk-OR$^{12}$, where Alk is present or absent and has the same meaning as above, and R$^8$ and R$^{12}$ have the same meaning as above, and R$^{12}$ is also hydrogen or $C_{1-20}$ alkylcarbonyl;

(3)

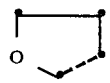

where the dashed bond replaces the 17α hydrogen;
(4) α-hydrogen and

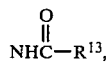

where R$^{13}$ is,
(a) $C_{1-12}$ alkyl; or
(b) NR$^9$R$^{10}$;
(5) α-hydrogen and cyano; or
(6) α-hydrogen and tetrazolyl; and pharmaceutically acceptable salts of the above compounds.

2. A compound of claim 1 of the formula:

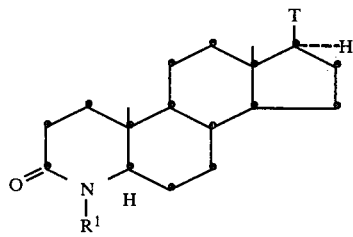

wherein R$^1$ is hydrogen, methyl, or amino; and T is CONHCH$_2$CH$_3$,

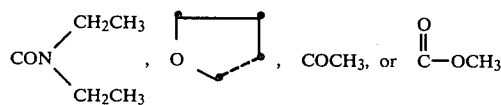

3. A compound of claim 1 wherein R$^1$ is methyl and T is CONHCH$_2$CH$_3$ or CON(CH$_2$CH$_3$)$_2$.
4. A compound of claim 1 wherein the compound is 17β-N,N-diethylcarbamoyl-4-methyl-4-aza-5α-androstan-3-one.
5. A compound of claim 1 wherein the compound is 17β-N,N-diethylcarbamoyl-4-aza-5α-androstan-3-one.
6. A compound of claim 1 wherein the compound is 17β-N,N-diethylcarbamoyl-4-amino-4-aza-5α-androstan-3-one.
7. A compound of claim 1 wherein the compound is 4-aza-5α-20-spiroxan-3-one.

8. A compound of claim 1 wherein the compound is 4-methyl-4-aza-5α-20-spiroxan-3-one.
9. A compound of claim 1 wherein the compound is 17β-N-ethylcarbamoyl-4-methyl-4-aza-5α-androst-3-one.
10. A compound of claim 1 wherein the compound is 4-methyl-4-aza-5α-pregnane-3,20-dione.
11. A compound of claim 1 wherein the compound is 20-hydroxymethyl-4-methyl-4-aza-5α-pregnane-3-one.
12. A compound of claim 1 wherein the compound is 17β-carbomethoxy-4-methyl-4-aza-5α-androstan-3-one.
13. A compound of claim 1 wherein the compound is 17β-N-octylcarbamoyl-4-methyl-4-aza-5α-androstane-3-one.
14. A method of treating the hyperandrogenic conditions of acne vulgaris, seborrhea, female hirsutism and benign prostatic hypertrophy comprising parenteral administration to a patient in need of such treatment of a therapeutically effective amount of a compound of formula:

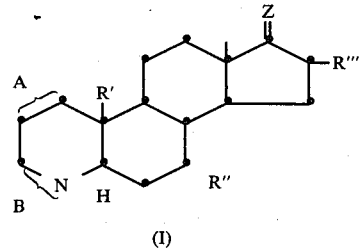

(I)

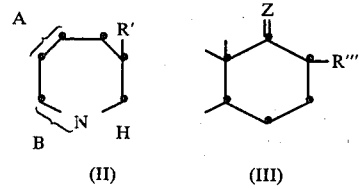

(II)          (III)

where Forumla (I) may also have the structure of partial Formulas (II) and/or (III);
wherein,
A is
(1) —CH$_2$—CH$_2$—;
(2) —CH=CH—;
(3)

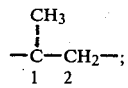

or
(4)

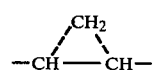

B is
(1)

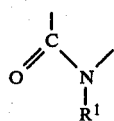

where
R$^1$ is,
(a) hydrogen;
(b) methyl or ethyl;
(c) ethenyl;
(d) ethynyl;
(e) NR$^2$R$^3$ where R$^2$ and R$^3$ are hydrogen or methyl; or
(f) cyano; or
(2)

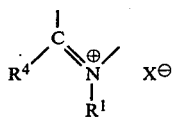

where X$^{\ominus}$ is any anion and R$^4$ is,
(a) OR$^5$ where R$^5$ is C$_{1-4}$alkyl; or
(b) NR$^6$R$^7$, where R$^6$ and R$^7$ are hydrogen or methyl;
R' is hydrogen or methyl;
R" is hydrogen or $\beta$-methyl;
R''' is hydrogen, $\beta$-methyl or hydroxyl;
Z is
(1) $\alpha$-hydrogen or $\alpha$-hydroxyl and
(a)

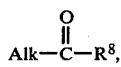

where Alk is present or absent and is straight or branched hydrocarbon chain of 1 to 12 carbon atoms; and R$^8$ is,
(i) hydrogen,
(ii) hydroxyl,
(iii) C$_{1-4}$alkyl
(iv) NR$^9$R$^{10}$, where R$^9$ and R$^{10}$ are each independently selected from hydrogen, C$_{1-4}$ straight or branched chain alkyl, C$_{3-6}$ cycloalkyl, phenyl; or R$^9$ and R$^{10}$ taken together with the nitrogen to which they are attached represent a 5-6 membered saturated ring comprising up to one other heteroatom selected from oxygen and nitrogen; or
(v) OR$^{11}$, where R$^{11}$ is M, where M is hydrogen or alkali metal, or C$_{1-18}$ straight or branched chain alkyl; benzyl; or
(b) Alk-OR$^{12}$, where Alk is always present and has the same meaning as above, and R$^{12}$ is
(i) phenyl C$_{1-6}$ alkylcarbonyl,
(ii) C$_{5-10}$ cycloalkylcarbonyl,
(iii) benzoyl, or
(iv) C$_{1-8}$ alkoxycarbonyl;
(v) amino, or C$_{1-8}$ alkyl substituted amino, carbonyl; or
(vi) hydrogen, provided that Alk is a branched C$_3$-C$_8$ chain;
(2)

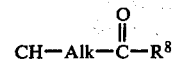

or CH-Alk-OR$^{12}$, where Alk is present or absent and has the same meaning as above, and R$^8$ and R$^{12}$ have the same meaning as above, and R$^{12}$ is also hydrogen or C$_{1-20}$ alkylcarbonyl;
(3)

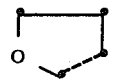

where the dashed bond replaces the 17$\alpha$ hydrogen;
(4) $\alpha$-hydrogen and

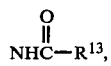

where R$^{13}$ is,
(a) C$_{1-12}$ alkyl; or
(b) NR$^9$R$^{10}$;
(5) $\alpha$-hydrogen and cyano; or
(6) $\alpha$-hydrogen and tetrazolyl; and pharmaceutically acceptable salts of the above compounds.

15. The method of claim 14 wherein there is employed a compound of formula:

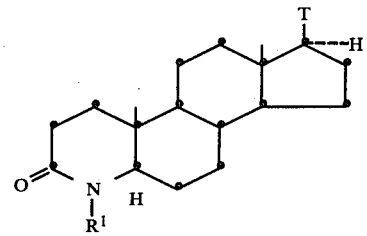

wherein R$^1$ is hydrogen, methyl, or amino; and T is

16. A method of inhibiting testosterone-5$\alpha$-reductase in a patient in need of such inhibiting treatment, comprising administration to such a patient of a therapeutically effective amount of a compound of the formula:

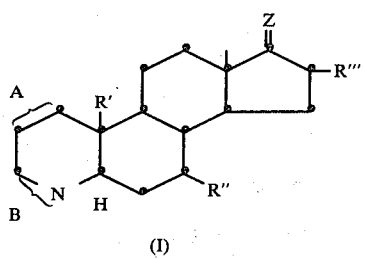

(I)

-continued (II) (III)

where Formula (I) may also have the structure of partial Formulas (II) and/or (III);
wherein,
A is
(1) —CH$_2$—CH$_2$—;
(2) —CH=CH—;
(3)

$$-\underset{\underset{2}{1}}{\overset{CH_3}{\underset{|}{C}}}-CH_2-;$$

or
(4)

$$-CH\underset{\diagdown}{\overset{CH_2}{\diagup}}CH-$$

B is
(1)

where
R$^1$ is,
(a) hydrogen;
(b) methyl or ethyl;
(c) ethenyl;
(d) ethynyl;
(e) NR$^2$R$^3$ where R$^2$ and R$^3$ are hydrogen or methyl; or
(f) cyano; or
(2)

where X$^\ominus$ is any anion and R$^4$ is,
(a) OR$^5$ where R$^5$ is C$_{1-4}$alkyl; or
(b) NR$^6$R$^7$, where R$^6$ and R$^7$ are hydrogen or methyl;
R' is hydrogen or methyl;
R'' is hydrogen or β-methyl;
R''' is hydrogen, β-methyl or hydroxyl;
Z is
(1) α-hydrogen or α-hydroxyl and
(a)

$$Alk-\overset{O}{\underset{\|}{C}}-R^8,$$

where Alk is present or absent and is straight or branched hydrocarbon chain of 1 to 12 carbon atoms; and R$^8$ is,
(i) hydrogen,
(ii) hydroxyl,
(iii) C$_{1-4}$alkyl
(iv) NR$^9$R$^{10}$, where R$^9$ and R$^{10}$ are each independently selected from hydrogen, C$_{1-4}$ straight or branched chain alkyl, C$_{3-6}$ cycloalkyl, phenyl; or R$^9$ and R$^{10}$ taken together with the nitrogen to which they are attached represent a 5-6 membered saturated ring comprising up to one other heteroatom selected from oxygen and nitrogen; or
(v) OR$^{11}$, where R$^{11}$ is M, where M is hydrogen or alkali metal, or C$_{1-18}$ straight or branched chain alkyl; benzyl; or
(b) Alk-OR$^{12}$, where Alk is always present and has the same meaning as above, and R$^{12}$ is
(i) phenyl C$_{1-6}$ alkylcarbonyl,
(ii) C$_{5-10}$ cycloalkylcarbonyl,
(iii) benzoyl, or
(iv) C$_{1-8}$ alkoxycarbonyl;
(v) amino, or C$_{1-8}$ alkyl substituted amino, carbonyl; or
(vi) hydrogen, provided that Alk is a branched C$_3$-C$_8$ chain;
(2)

$$CH-Alk-\overset{O}{\underset{\|}{C}}-R^8$$

or CH-Alk-OR$^{12}$, where Alk is present or absent and has the same meaning as above, and R$^8$ and R$^{12}$ have the same meaning as above, and R$^{12}$ is also hydrogen or C$_{1-20}$ alkylcarbonyl;
(3)

where the dashed bond replaces the 17α hydrogen;
(4) α-hydrogen and $$NH\overset{O}{\underset{\|}{C}}-R^{13},$$

where R$^{13}$ is,
(a) C$_{1-12}$ alkyl; or
(b) NR$^9$R$^{10}$;
(5) α-hydrogen and cyano; or
(6) α-hydrogen and tetrazolyl; and pharmaceutically acceptable salts of the above compounds.

17. The method of claim 16 wherein there is employed a compound of formula:

wherein R¹ is hydrogen, methyl, or amino; and T is $$CON\begin{matrix}CH_2CH_3\\CH_2CH_3\end{matrix}\ ,\ \langle O \rangle\ ,\ COCH_3,\ \text{or}\ \overset{O}{\underset{\|}{C}}-OCH_3$$

18. A pharmaceutical composition comprising a pharmaceutically acceptable carrier and a compound of formula:

(I)

where Formula (I) may also have the structure of partial Formulas (II) and/or (III);
wherein,
A is
   (1) —CH₂—CH₂—;
   (2) —CH=CH—;
   (3)

$$-\underset{\underset{1}{\overset{|}{C}}}{\overset{CH_3}{|}}-CH_2-;$$

$\phantom{xx}$ 2 or
   (4)

$$-CH\underset{}{\overset{CH_2}{\diagup\diagdown}}CH-$$

B is
   (1)

$$\overset{|}{\underset{\underset{R^1}{|}}{C}}\diagdown\underset{O}{\overset{}{N}}$$

where
   R¹ is,
      (a) hydrogen;
      (b) methyl or ethyl;
      (c) ethenyl;
      (d) ethynyl;
      (e) NR²R³ where R² and R³ are hydrogen or methyl; or
      (f) cyano; or
   (2)

$$R^4\diagup\overset{|}{\underset{\underset{R^1}{|}}{C}}\diagdown\overset{\oplus}{N}\quad X^{\ominus}$$

where X⊖ *is any anion and R4* is,
   (a) OR⁵ where R⁵ is C₁₋₄alkyl; or
   (b) NR⁶R⁷, where R⁶ and R⁷ are hydrogen or methyl;
R' is hydrogen or methyl;
R" is hydrogen or β-methyl;
R'" is hydrogen, β-methyl or hydroxyl;
Z is
   (1) α-hydrogen or α-hydroxyl and
   (a)

$$Alk-\overset{O}{\underset{\|}{C}}-R^8,$$

where Alk is present or absent and is straight or branched hydrocarbon chain of 1 to 12 carbon atoms; and R⁸ is,
   (i) hydrogen,
   (ii) hydroxyl,
   (iii) C₁₋₄alkyl
   (iv) NR⁹R¹⁰, where R⁹ and R¹⁰ are each independently selected from hydrogen, C₁₋₄ straight or branched chain alkyl, C₃₋₆ cycloalkyl, phenyl; or R⁹ and R¹⁰ taken together with the nitrogen to which they are attached represent a 5-6 membered saturated ring comprising up to one other heteroatom selected from oxygen and nitrogen; or
   (v) OR¹¹, where R¹¹ is M, where M is hydrogen or alkali metal, or C₁₋₁₈ straight or branched chain alkyl; benzyl; or
   (b) Alk-OR¹², where Alk is always present and has the same meaning as above, and
R¹² is
   (i) phenyl C₁₋₆ alkylcarbonyl,
   (ii) C₅₋₁₀ cycloalkylcarbonyl,
   (iii) benzoyl, or
   (iv) C₁₋₈ alkoxycarbonyl;
   (v) amino, or C₁₋₈ alkyl substituted amino, carbonyl; or
   (vi) hydrogen, provided that Alk is a branched C₃–C₈ chain;

(2)

or CH-Alk-OR$^{12}$, where Alk is present or absent and has the same meaning as above, and R$^8$ and R$^{12}$ have the same meaning as above, and R$^{12}$ is also hydrogen or C$_{1-20}$ alkylcarbonyl;

(3)

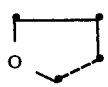

where the dashed bond replaces the 17α hydrogen;

(4) α-hydrogen and

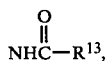

where R$^{13}$ is, (a) C$_{1-12}$ alkyl; or
(b) NR$^9$R$^{10}$;

(5) α-hydrogen and cyano; or
(6) α-hydrogen and tetrazolyl; and pharmaceutically acceptable salts of the above compounds.

19. The composition of claim 18 wherein there is employed a compound of formula:

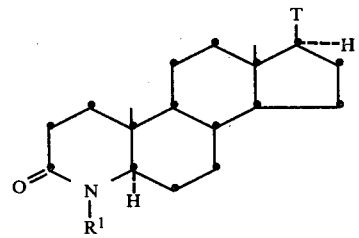

wherein R$^1$ is hydrogen, methyl, or amino; and T is